United States Patent [19]
Gui et al.

[11] Patent Number: 5,391,270
[45] Date of Patent: Feb. 21, 1995

[54] DETECTION AND MEASUREMENT OF HEAVY METALS

[75] Inventors: John Y. Gui, Schenectady; Donald F. Foust, Scotia, both of N.Y.

[73] Assignee: General Electric Company, Schenectady, N.Y.

[21] Appl. No.: 104,684

[22] Filed: Aug. 11, 1993

[51] Int. Cl.$^6$ .............................................. G01N 27/26
[52] U.S. Cl. .................. 204/153.1; 204/412; 204/434
[58] Field of Search ............ 204/153.1, 400, 412, 204/434

[56] References Cited

U.S. PATENT DOCUMENTS

| | | | |
|---|---|---|---|
| 3,329,599 | 7/1967 | Brewer | 204/415 |
| 4,090,926 | 5/1978 | Matson | 204/434 |
| 4,146,436 | 3/1979 | Kellermann et al. | 204/434 |

OTHER PUBLICATIONS

Kolthoff et al, *Polarography*, 2d. rev. ed., (1952), vol. 2, pp. 507–510.

*Primary Examiner*—T. Tung
*Attorney, Agent, or Firm*—James Magee, Jr.

[57] ABSTRACT

Disclosed herein is an improved method for measuring the presence and amount of a variety of metals contained in a sample. In the first step, all of the various forms of each metal are converted to a soluble metallic complex which is capable of being electrochemically reduced. Voltammetry is then used to determine the stripping current or charge characteristic of each metallic complex. Finally, the concentration of each metal can be calculated by insertion of the stripping current or charge value into an equation which correlates peak current or charge values with metal concentration.

The metals which can be detected and quantified by using this method are gold, silver, bismuth, cadmium, thallium, and mercury.

11 Claims, 2 Drawing Sheets

DETECTION AND MEASUREMENT OF HEAVY METALS

FIELD OF THE INVENTION

This invention generally relates to analytical techniques, and more particularly, to the electrochemical detection and measurement of certain metals in the course of site characterization, process monitoring and control and remediation of toxic waste materials.

BACKGROUND OF THE INVENTION

Many techniques are currently available for the detection of metals in the environment. The development and improvement of these techniques has become a major focal point of analytical science because of the growing need to detect very small amounts of metallic contaminants which adversely affect the environment. For example, mercury is regarded as a very toxic heavy metal, and its presence in soil and waterways represents a considerable health hazard. Government agencies throughout the world are thus increasing restrictions on the release of mercury to the environment. In some countries, a legislated limit of 2 parts-per-billion in drinking water has been enforced. Other potentially hazardous metals like lead and cadmium appear to be receiving the same scrutiny.

The most commonly used methods for detecting various metals are atomic absorption (AA), inductively coupled plasma atomic emission (ICP-AE), and mass spectroscopy (MS). Each of these methods is suitable for trace analysis of metals like mercury in a laboratory setting. However, they often require well-controlled experimental conditions, expensive instrumentation, and frequent maintenance and calibration. Moreover, these methods usually require lengthy sample preparation, especially when other interfering metals or impurities are present in the sample under investigation. For these reasons, the methods mentioned above are not particularly well-suited for rapid analysis in the field.

Other methods which are sometimes suitable for metal detection and analysis in the field include X-ray fluorescence (XRF), colorimetry, and ion-selective electrode (ISE). Special mention is made of XRF, which is used in the field because of its suitability for simultaneously detecting many metals without substantial sample preparation. However, the detection limits for this method (about 30–100 ppm for mercury in soil samples) are not low enough for accurately determining very low levels of metals like mercury. Moreover, XRF is very dependent on the nature of the environmental sample. For example, if one is running a mercury analysis on both a soil sample and a plastic sample, a separate calibration curve must be prepared for each.

Colorimetric techniques can be complicated and time-consuming. Also, such techniques are often very specific, e.g., selective to only one type of mercury complex.

ISE is a useful detection tool in some instances, but it is usually limited to the detection of inorganic ions. Furthermore, measurement is heavily dependent upon the specific composition of a sample substrate, since the potentiometric response varies not only with the particular metal being investigated, e.g., mercury, but also with varying concentrations of halides and sulfides which may constitute part of the substrate.

Because of its high sensitivity, Anodic Stripping Voltammetry (ASV) is a very popular laboratory tool for the detection of heavy metals. However, the method is not typically used for mercury because mercury is the preferred working electrode in ASV. The limitation of this method in field analysis, especially for solid wastes, is mainly due to lack of fast extraction of metals to an aqueous solution and the deactivation of working electrode.

SUMMARY OF THE INVENTION

In view of the limitations of the prior art, an improved method for detecting and measuring various metals in the environment is desirable. The present invention describes such a method, and comprises the steps of:

a) converting all species of each metal being measured in the sample to a soluble metallic complex which is capable of being electrochemically analyzed;

b) determining the stripping peak current and charge signals characteristic of each metallic complex by voltammetric means in a complex-ligand based solution; and then c) calculating the level of each metal by substituting its characteristic stripping signal value into the formula $$C = \left(\frac{1}{K}\right)Y + A$$

wherein C is the concentration (ppm) of the particular metal in the voltammetric solution prepared for the sample; K and A are the precalculated slope and constant of a voltammetric calibration curve which plots stripping signal as a function of known concentrations of the particular metal; and Y is the peak stripping current (uA) or charge value (uC) observed in step (b) for the particular metal. The method can be used for metals which are nonreactive with water, and which can be analyzed by voltammetry in the iodide-based solution.

This method is characterized by speed, sensitivity, simplicity, selectivity and accuracy, and is therefore of great use in the field. It is useful for detecting the presence of a particular metal, as well as measuring how much of the metal is present. It can be used to detect heavy metals such as lead, cadmium, chromium, iron or/and nickel individually and simultaneously.

Another embodiment of this invention relates to the detection and measurement of multiple metals in a liquid or solid sample, as described below.

DETAILED DESCRIPTION OF THE INVENTION

Figure 1:
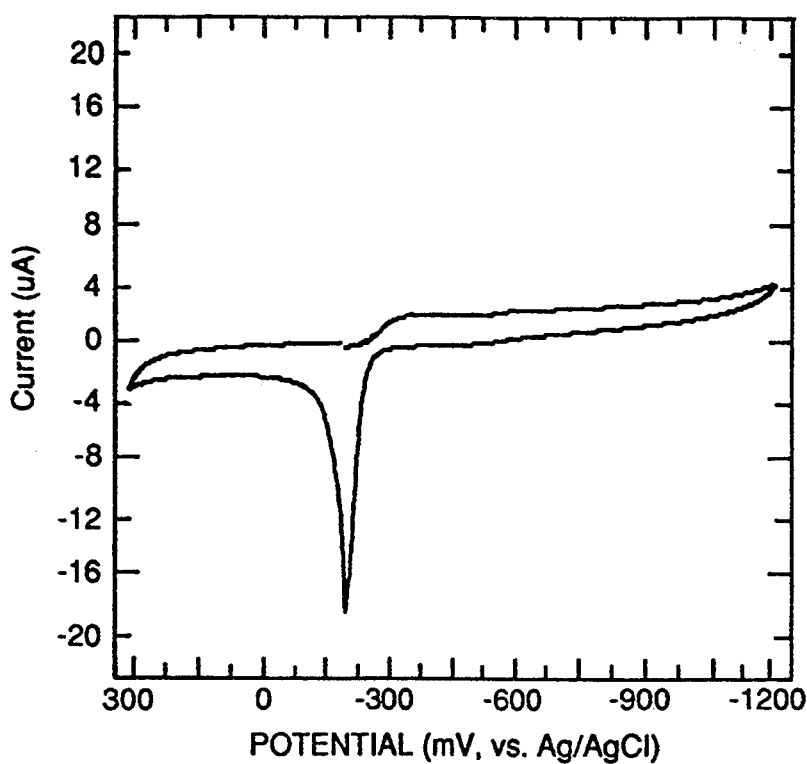
FIG. 1 is a cyclic voltammogram for a sample containing mercury.

The method of this invention is based on anodic stripping electroanalysis for metal ions in an aqueous solution. For solid samples of toxic metal-contaminated materials an extraction process is used to transfer the metal species from the solid substrate to an aqueous phase. In the case of mercury, a potassium iodide-iodine ($KI/I_2$) solution is used to extract different mercury species from the solid substrate, e.g., polymer, soil, brick, or concrete, into the iodide/iodine solution. Square wave, differential pulse or linear-scan anodic stripping is then used to complete the electroanalysis. Due to the strong mercury iodide complex $(HgI_x)^{2-x}$ which is formed, the extraction, solubilization of the mercury is essentially complete. The analytical method is non-destructive, reproducible, and rapid. Other metals in the solution do not interfere and atmospheric oxygen in the iodide/iodine solution has essentially no effect on the analysis. The detection limit of the method is about 20 parts per trillion. The present invention is suitable for the detection and measurement of metals which are nonreactive with water, and which can be converted into an iodide-based complex capable of being electrochemically reduced. Examples of such metals are gold, silver, bismuth, cadmium, thallium, and mercury. The metals may be contained in a solid sample, such as soil or a plastic-containing mixture or material.

The metals being detected are first extracted from environmental samples of contaminated soil or other material by a technique which converts all species of the metal in the sample to a soluble metallic complex which is capable of being electrochemically reduced. Extraction techniques are generally known in the art.

In a preferred embodiment of the invention, the metal contaminant is extracted into a iodine-iodide solution, e.g. a 1 molar potassium iodide, 0.5 molar iodine solution.

The extracting solution itself need not be an iodide solution, but is preferably so because of its speed and effectiveness in the extraction.

The cationic portion of the iodide-metal complex is not particularly critical, as long as it is water-soluble. Examples of suitable cations are sodium, potassium, ammonium, and calcium. In general, the preferred iodine-based complexes for use in this method are potassium iodide and sodium iodide with potassium iodide, being most preferred. The concentration of the solution itself is usually in the range of about 0.01 to about 10M in water, and more preferably, in the range of about 0.1 to about 1M.

The amount of extracting solution employed will depend on various factors, such as the solubility of the metals being detected and the form of the environmental sample. The amount should be that which is capable of reacting with all species of the particular metal present and redistributing the metal from the solid phase to the liquid phase. The most efficient concentration of extractant can be determined experimentally, e.g., by isolating portions of the sample and analyzing the metal content in the sample by a conventional method such as atomic absorption, and then comparing that measurement with trial-determinations of the present technique at various extractant concentrations. Typically, about 2-100 parts extracting solution are employed per 1 part of sample by weight. The solution is usually shaken or stirred, although this is not critical.

After each of the metal species has been converted to an electrochemically-reducible complex, the stripping response value for each complex is determined by voltammetry. Voltammetric techniques are well-known in the art, and are described, for example, in the Kirk-Othmer Encyclopedia of Chemical Technology, Third Edition, Volume 2 (1978), pp 618-619; as well as in Fundamentals of Analytical Chemistry, D. Skoog and D. West, Third Edition, Holt, Rinehart and Winston (1976), pp 463-498. All of these techniques, which utilize an electrolytic cell, measure the current-voltage behavior of a working electrode in a system which also contains a nonpolarizable reference electrode, an auxiliary electrode and a large excess of electrolyte, e.g., the iodide-containing solution described above.

Examples of voltammetric techniques (which are also sometimes referred to as "polarographic" procedures) are differential pulsed voltammetry, linear scan polarography, AC polarography, rapid scan polarography, cyclic voltammetry ("CV"), square-wave voltammetry and stripping voltammetry, e.g., anodic stripping voltammetry ("ASV"). While CV and ASV are the preferred techniques for this step of the invention, it is believed that those of ordinary skill in the electroanalytical arts can use or modify any of the techniques listed above to derive the desired voltammogram which is described below. CV is often the preferred procedure for initially screening a sample to determine approximately what level the metals under investigation is present in the sample. ASV is very suitable for the quantitative analysis of metals, especially when they may be present at very low levels.

Using ASV as an exemplary technique, the electrolytic cell would include a working electrode, a reference electrode, and an auxiliary electrode, along with the iodide-based electrolyte described above.

Any commonly used working electrode is suitable, as long as it is electrically conductive, has an adequate potential range and will not dissolve in or react with the electrolyte when voltage is applied. Illustrative examples include gold, platinum, glassy-carbon, and conventional carbon fiber. Gold is the most preferred material of choice, while glassy carbon can also be used. A microelectrode is often preferred when an analysis of sub-microliter size samples is required.

The type of reference electrode is important, particularly for field analysis which requires electrode stability and accuracy. A particularly preferred reference electrode is a silver wire coated with a layer of silver iodide immersed in 0.1M potassium iodide solution presaturated with silver iodide. The auxiliary electrode is usually a metal wire such as platinum.

For a sensitive technique such as ASV, it is sometimes useful to dilute the sample by a factor of, for example, 10- or 100-times its initial volume, using either more of the electrolyte or purified water. This dilution step can significantly reduce the matrix interference for metal analysis.

ASV most often includes at least three steps. First, an initial potential is applied to the working electrode to obtain a clean, reproducible electrode surface. Second, the electrode potential is adjusted to a negative potential which causes the ions of the metal being investigated to be reduced to a metallic state and to be deposited on the electrode surface, regardless of the initial species of the metal. Deposition time will vary from a few seconds to hours, depending on the amount of the metal contained in the solution. Generally, as the deposition time increases, the sensitivity of the entire process increases, i.e., much lower levels of a particular metal can be detected. Thus, while a short deposition time is usually sufficient for rapid field analysis for metals in the concentration range of about 1 ppm-100 ppm, deposition times in the range of about 1 to 10 minutes can often detect metals at concentrations in the parts-per-billion (ppb) range, while longer deposition times can detect metal concentrations in the parts-per-trillion (ppt) range. The overall deposition time can be shortened by the use of multiple electrodes simultaneously. The electrolyte solution may be stirred during this step to accelerate deposition on the electrode, but the stirring must be carried out consistently for the calibration samples and the test samples.

The optimal deposition potential can be revealed by trial settings and examination of the resulting voltammograms. Different working electrode material yields different deposition potential profile. Presence of other interfering components in solutions can greatly alter the potential profile, too. Using detection of mercury in a potassium iodide solution at a glassy carbon electrode as an illustration, the deposition potential is usually in the range of about −0.4 V to about −1.8 V, vs. Ag/AgI reference electrode, and most often, in the range of about −0.6 V to about −1.2 V. Stripping current and charge both increase as the deposition potential shifts toward more negative values. When the potential exceeds about −1.4 V for the mercury-containing system, the stripping signal tends to decrease as a result of vigorous hydrogen gas evolution at the electrode surface. The above deposition potential profile obtained from mercury standard solution may be not applicable for environmental samples because they may contain other metals. If the potential is set at too negative a value, other metals may codeposit with mercury, forming intermetallic compounds which could complicate the electroanalysis.

In contrast to the deposition potential profile at the glassy carbon electrode, deposition potential between 0.0 to −0.6 V for Hg electroanalysis at gold electrode has essentially no effect on the stripping results. This is due to the strong surface Au-Hg amalgamation and I-Au chemisorption. During the course of Hg deposition at the iodine-preadsorbed electrode surface, a place exchange between deposited Hg atom and adsorbed iodine may take place. The iodine layer at the Au surface plays a very important role because it protects the electrode from deactivation caused by surface contamination and selectively filters Hg into its layer to avoid Hg interaction into other species in solution.

Since stripping signals appear to be substantially independent of the concentration of the iodide-based electrolyte solution, the iodide concentration is not particularly critical. Usually, the concentration is in the range of about 0.0001M to about 10M in water. In the case of mercury, a preferred concentration is often in the range of about 0.001M to about 1.0M. As described in an example which follows, the iodide concentration can be varied to shift the stripping peak in the resulting voltammogram, thereby avoiding any potential overlap with other metals. This convenient shift does not have any effect upon the final determination of metal concentration.

In the third step, the working electrode is subjected to a positive potential scan in order to oxidize ("strip off") the metal from the electrode surface back into the solution. As a result of this scan, an anodic stripping current is produced. Its maximum or peak value or charge is used in the calculation of metal concentration, as further described below.

Electrical potential for this invention can generally be adjusted and maintained by any technique familiar in the art. Potentiostats are well-known devices which are very useful for this purpose, as described in the Skoog et al reference previously discussed. These devices can of course be computer-controlled to insure accuracy and reproducibility of measurement and to provide simplicity and automation of operation and convenience of data storage and handling.

The positive potential scan may be carried out in a variety of modes, e.g., linear, differential pulsed, or square wave pattern. Selection is determined by the resolution and sensitivity required and the desired speed of the scan. For example, mercury analysis is very quickly carried out, with acceptable resolution, using a linear scan. Higher resolution of other metals can be obtained by the pulsed or square wave pattern.

FIG. 1 depicts an illustrative cyclic voltammogram for mercury, using a glassy carbon disc 1 mm in diameter as the working electrode. 100 ppm mercury, in the form of mercury iodide, had been dissolved in a 0.1M potassium iodide electrolyte solution. The solution had been deoxygenated with nitrogen prior to application of a linear potential scan. The electrochemical cell was maintained at room temperature and occupied a volume of about 3 ml; the auxiliary electrode was platinum wire, and the reference electrode was a silver wire coated with silver chloride immersed in a solution of silver chloride saturated 3M potassium chloride. The scanning rate was 200 mV/s. The figure clearly shows a very distinct stripping current-peak of about −17 microamps (uA).

As mentioned above, the stripping current value for a particular metal is proportional to the concentration of that metal in the sample being analyzed. This linear relationship is first established by preparation of a standard, "calibration" curve for the particular metal, by performing ASV (or any other voltammetric technique being used) in the same electrolyte solution for known concentrations of mercury.

Figure 2:
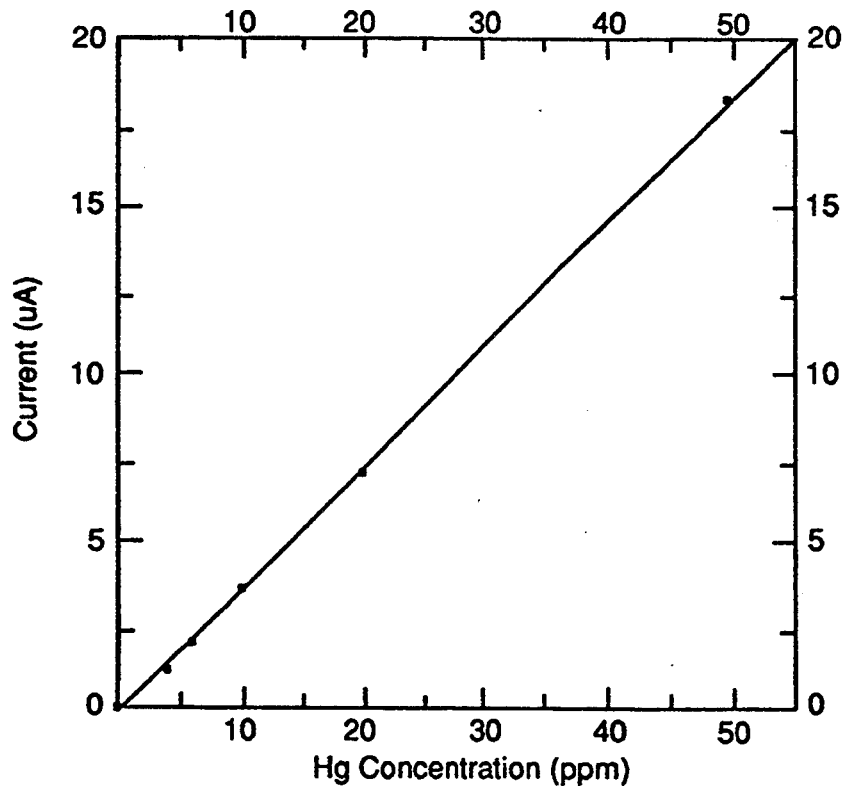
FIG. 2 is a calibration curve for a mercury-containing sample subjected to voltammetric analysis.

FIG. 2 depicts an illustrative calibration curve for a mercury-containing sample, utilizing cyclic voltammetric analysis. The stripping currents were measured for various standard concentrations of mercury. The electrolyte solution was 0.1M potassium iodide. The cyclic scan began at 0.0 V and covered the range of −1200 mV to 200 mV, with a scan rate of 300 mV/s. The electrochemical cell volume was 3 ml, and the solution was maintained at room temperature. The working electrode was a glassy carbon disc, 1 mm in diameter. The auxiliary electrode was a platinum wire; while the reference electrode was a silver wire immersed in a solution of silver chloride and 3M potassium chloride. None of the test solutions was deoxygenated.

FIG. 2 clearly demonstrates a linear relationship between maximum stripping current values and concentrations for a particular metal. The amount ("C") of metal contained in a particular sample can then be calculated according to the equation $$C = \left(\frac{1}{K}\right)Y, \tag{I}$$

wherein C is the concentration (ppm) of the particular metal in the voltammetric solution prepared for the sample; K is the precalculated slope for a calibration curve like that of FIG. 2; and Y is the peak stripping current value (uA) determined by way of a voltammogram like that depicted in FIG. 1.

The method of this invention can be used to determine the concentration of several metals of interest, as mentioned above, since they all can be extracted from the environment with an iodide-based solution. In one exemplary embodiment for detecting three such metals, e.g., gold, cadmium, and mercury, an environmental sample would first be divided into three portions. Each portion would then be separately mixed with a suitable extractant capable of reacting with and solubilizing all of the particular metal under examination, as described above. The extractant/metal solutions can then be put into separate electrolytic cells for voltammetric analysis, or else the same cell may be used in successive runs if it is cleaned and rinsed between runs.

Standard calibration curves for each of the metals are calculated through the stripping experiments. As described above, the slope value for these curves is inserted into Equation I, along with the peak stripping current obtained by voltammetry, for calculation of the concentration of each metal in the sample.

In an alternative embodiment, several (or all) of the metals mentioned above can be detected simultaneously. Portions of a sample containing the metals are first used to calculate calibration curves for each metal under investigation. The main body of the sample is then reacted with a suitable extractant, followed by voltammetric analysis on the resulting solution. Since it is believed that each of the metals mentioned above has a separate and distinct stripping peak, identification of the corresponding current value for the metal should be possible without undue effort. If there appears to be any overlap in stripping peaks, the concentration of the iodide-based solution can be adjusted to shift one or more of the peaks, thereby permitting easier measurement of each peak. As described above, the final calculations for each metal are based on Equation I, supra.

In summary, the method of the present invention has many advantages. First, it is simple, with only a one-step extraction and one-step voltammetric analysis being required after calibration. Second, the method can be carried out quickly, with extraction times of only about 5 to 30 minutes, and stripping times which can be as short as 5 seconds when detecting the presence of a particular metal. Third, the method is very selective since both extraction and ASV analysis are metal-specific. Fourth, the method can be portable, a battery-operated electroanalytical unit can be used in the field.

Yet another advantage of this method is its accuracy. The metals listed above exhibit very distinct stripping peaks during voltammetry, thereby minimizing interference from other metals which might complicate the calculation of concentration. Furthermore, potassium iodide and iodine concentrations have very little effect on stripping current intensity, thereby minimizing problems which might occur when iodine consumption varies with different samples. The examples demonstrate this accuracy, with quantitative results often within about 10% of results obtained with more complex laboratory techniques such as atomic absorption.

Moreover, the method is reliable in the field for several reasons. First, it is insensitive to presence of atmospheric oxygen in solution and to impurities and other constituents in the sample matrix. Second, the electrode assembly is very durable, and has a very long operation lifetime.

Furthermore, the method can be used for the detection of more than one metal, thereby greatly increasing its usefulness for wide-scale field analysis, as described above.

The following examples are provided to more fully describe this invention. They should be considered as illustrative of what is disclosed and claimed herein.

EXAMPLE 1

In this example, the concentration of the iodide-based solution in an electrolytic cell was varied to demonstrate that the stripping potential for the voltammetric step of this invention can be adjusted without adversely affecting the determination of metal concentration. 5 ppm portions of mercury (in the form of $HgI_2$) were dispersed in potassium iodide (KI) solutions of three different concentrations (in water): 25 mM, 10 mM, 50 mM, 100 mM, and 500 mM. To maintain the same electrolyte strength, the solutions were each mixed with 0.25M potassium sulfate, forming the electrolyte of an electrolytic cell for cyclic voltammetry. The 500 mM solution was used for the same purpose, but did not include any potassium sulfate. The working electrode was a glassy carbon disk, 1 mm in diameter. The auxiliary electrode was a platinum wire, while the reference electrode was a silver wire coated with a layer of silver iodide immersed in a 0.1M potassium iodide solution which is saturated with silver iodide.

The cathodic limit of all cyclic scans was set at $-1240$ mV in a direction more negative than the stripping peak potential, while the anodic limit was set at 260 mV in a direction more positive than the peak potential.

The voltammetric scan rate was 200 mV/s; and all solutions were deoxygenated.

Figure 3:
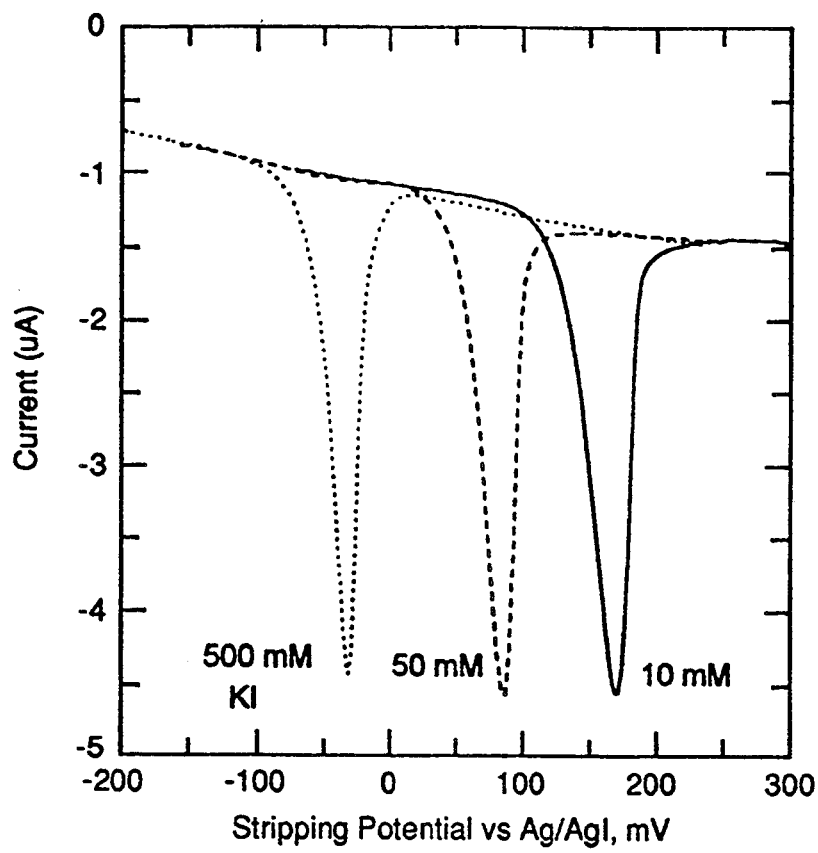
FIG. 3 is a portion of cyclic voltammogram which includes stripping current values for varying potassium iodide concentrations.

FIG. 3 is a graphical representation of three of the resulting voltammograms. It is clear from the graph that the stripping peak can readily be shifted without substantially changing the peak current value.

Furthermore, when the resulting stripping peaks were plotted against log potassium iodide concentration, the resulting slope had a theoretical value of 117 mV, which was in close agreement with the theoretical value of 118 mV (based on the Nernst equation).

In an ancillary experiment, stripping was performed in the same manner at the various potassium iodide concentrations, for two different sets of mercury-containing solutions: one with all oxygen removed by nitrogen purging, and the other retaining the oxygen.

A resulting graph of stripping current as a function of potassium iodide concentration (expressed in logarithmic form) demonstrated that the presence of oxygen dissolved in the sample solution had no effect on stripping current values. This attribute represents a considerable advantage because it eliminates the need for time-consuming deoxygenation procedures.

EXAMPLE 2

A comparison was undertaken between mercury detection by way of a prior art technique, atomic absorption(AA), and a technique according to the present invention, anodic stripping voltammetry (ASV). 14 of the samples were from the field, i.e., having undetermined mercury content; while 10 of the samples were soil doped with known amounts of various species of mercury.

One gram of sample was mixed with 10 mL of 1.0 MKI/0.5 $MI_2$ and heated in a sealed vessel for 30 minutes at 100° C. The vessel was cooled and filtered. The filtrate was analyzed by ASV.

For ASV, the working electrode was a gold disk, 1 mm in diameter; and the auxiliary electrode was a platinum wire. The reference electrode was the same type used in example 1.

The electrolyte was 0.1M potassium iodide, 0.005M iodine, and 0.25M potassium sulfate. The electrochemical cell volume was 3 ml. None of the solutions was deoxygenated or stirred during deposition and stripping.

Voltammetric deposition was carried out at −100 mV for either 5, 30 or depending the Hg concentration in solution 600 seconds, followed by 5.5 or 10 seconds, respectively, at 0.0 mV prior to square-wave anodic stripping.

The mercury concentrations were obtained by comparing the experimentally-determined peak stripping charge or current with a corresponding calibration curve for the sample. The values in the table represent mercury concentration in solid samples, not in the dilute extract which would be values 1000 times as small.

Samples 1-6, 10-13, and 21-24 were taken from the field. The source is indicated in Table 1. "Phenolic" indicates phenol/formaldehyde-based plastic. The remaining samples were doped with various forms of mercury. The results were as follows:

TABLE 1

| Sample No. | Media | Form of Hg | Hg by AA* (ppm) | Hg by ASV** (ppm) |
|---|---|---|---|---|
| 1 | Phenolic | Unknown | 623 | 477.4 |
| 2 | " | " | 11 | 9.1 |
| 3 | " | " | 52 | 33.5 |
| 4 | " | " | 138 | 102.4 |
| 5 | " | " | 303 | 138.2 |
| 6 | " | " | 623 | 633.1 |
| 7 | Soil | $Hg^0$ | 100 | 114.0 |
| 8 | " | $Hg^0$ | 1000 | 989.1 |
| 9 | " | $Hg^0$ | 10000 | 8742.0 |
| 10 | " | None | Not detected | Not detected |
| 11 | " | HgS | 3347 | 3125.0 |
| 12 | " | " | 113 | 92.4 |
| 13 | " | $Hg^0$ | 6217-32000*** | 22678.0 |
| 14 | " | $Hg_2O$ | 955 | 950.2 |
| 15 | " | HgS | 1007 | 889.0 |
| 16 | " | $(Hg)_3(PO_4)_2$ | 1102 | 994.7 |
| 17 | " | $HgCl_2$ | 941 | 1000.0 |
| 18 | " | $Hg_2O$ | 1099 | 749.9 |
| 19 | " | $Hg_2Cl_2$ | 984 | 1123.0 |
| 20 | " | $CH_3HgCl$ | 240 | 266.1 |
| 21 | Phosphor | $Hg^0$ | 3666 | 4037.0 |
| 22 | " | $Hg^0$ | <10 | <5.0 |
| 23 | Brick | $Hg_0$ | 3080# | 4804.0 |
| 24 | Concrete | $Hg^0$ | 1164 | 1006.0 |

*AA = Atomic Absorption
**ASV = Anodic Stripping Voltammetry
*** = The sample contains visible Hg beads, thus there is a large Hg concentration variation due to sampling.
# = estimated value.

The data generally demonstrate a close correlation between results for AA and for ASV, especially in the samples of soil, phosphor, brick, and concrete. The results for the phenol samples were not as reproducible, although they still demonstrate very rapid measurement of mercury with some degree of accuracy. Variable reproducibility for the phenolic samples may be due to deactivation of the gold electrode surface as a result of strong absorption of organic species which existed in the phenolic material. It has been demonstrated that more reproducible and accurate results for the phenolic samples can be obtained if the working electrode is cleaned before each run. Cleaning of gold electrode can be performed by electrochemical oxidation-reduction cycling in an acidic solution. Glassy carbon electrode can be cleaned by either ultrasonication in an acidic solution or mechanic polishing.

EXAMPLE 3

In this experiment, sample solutions were prepared on a laboratory scale. The samples were not extracted from the environment. Sample A contained 1.00 ppm lead (Pb) and 1.00 ppm cadmium (Cd) in a 0.1M KI solution, while sample B contained 1.00 ppm each of Pb, Cd, and mercury (Hg) in a 0.1M KI solution. An electrolytic cell was prepared for square-wave anodic stripping, using each solution as the electrolyte. A glassy carbon working electrode (1 mm disc shape) was employed, as described above. The auxiliary electrode was platinum wire, while the reference electrode was the same type used in example 1. All solutions were deoxygenated.

Figure 4:
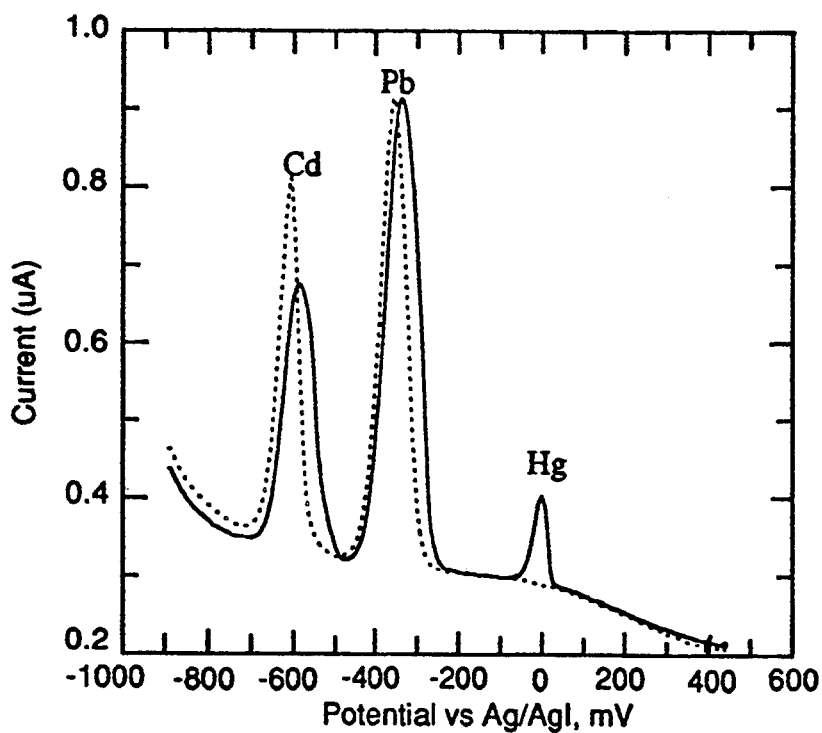
FIG. 4 is a voltammogram based on a sample which contained several metals.

Deposition was carried out for 1 second at −900 mV in a steady-state solution followed by stripping under the following conditions:
Amplitude: 30 mV
Step height: 2 mV
Period: 30 ms FIG. 4 depicts the resulting voltammogram, with sample A represented by the dotted line and sample B represented by the solid line. While lead is not one of the metals which is thought to be extractable with the iodide-based solution of this invention, the figure does demonstrate that mercury and cadmium can be simultaneously detected and quantified. This detection would not be impeded by the presence of lead, which clearly exhibits its own distinct stripping peak.

EXAMPLE 4

The sensitivity and accuracy of the ASV (Anodic Stripping Voltammetry) methodology and XRF (X-Ray fluorescence) commercially available are compared. The results are listed in Table 2 below along with the results from the analytical lab using AA method. The comparison clearly demonstrated that ASV has much higher (at least two orders of magnitude) sensitivity than the XRF and has less substrate interference as illustrated by the sample 11/4/03, for which the XRF result is one order of magnitude smaller than the AA value while the ASV result is very close to the AA value.

TABLE 2

| | COMPARISON BETWEEN AA, ASV AND XRF RESULTS FOR MERCURY ANALYSTS | | | | | |
|---|---|---|---|---|---|---|
| Sample # | Source | Media | Hg Form | AA ppm | ASV ppm | XRF ppm |
| 11/4/01 | Real | Soil | — | ND* < 3 | ND < 2 | ND < 30 |
| 11/4/02 | Real | Phenolic | ? | 429.0 | 288.3 | 1054 |
| 11/4/03 | Real | Phosphors | Hg | 3666.0 | 4037 | 345 |
| 11/4/04 | Doped | Soil | Hg | 100.0 | 114 | 135 |
| 11/4/05 | Real | Phenolic | ? | 52.0 | 33.5 | 104 |

TABLE 2-continued

COMPARISON BETWEEN AA, ASV AND XRF RESULTS FOR MERCURY ANALYSTS

| Sample # | Source | Media | Hg Form | AA ppm | ASV ppm | XRF ppm |
|---|---|---|---|---|---|---|
| 11/4/06 | Doped | Solution | $HgI_4{}^{2-}$ | NA** | 40*** | |
| 11/4/07 | Doped | Solution | $HgI_4{}^{2-}$ | NA | 200*** | 392 |
| 11/4/08 | Doped | Solution | $HgI_4{}^{2-}$ | NA | 0.04*** | ND < 3 |

*ND = Not Detectable
**NA = Not Analyzed
***Standard solution

Other modifications and variations of this invention are possible in view of the description thus provided. It should be understood, therefore, that changes may be made in the particular embodiments shown which are within the scope of the invention defined in the appended claims.

What is claimed is:

1. A method for rapidly measuring the amount of a metal contained in sample, said metal being nonreactive with water, comprising the steps of:
   a) converting all species of the metal in the sample being measured to a soluble metallic complex which can be electrochemically analyzed, by extracting the metal with an iodine/iodide solution;
   b) voltammetrically determining the peak stripping current value for the metallic complex in the iodine/iodide solution; and then
   c) calculating the level of metal by substituting the stripping current value into the formula $$C = \left(\frac{1}{K}\right)Y + A$$

wherein C is the concentration of the metal in the solution prepared for the sample; K and A are is the precalculated slope and constant of a voltammetric calibration curve which plots stripping current as a function of known concentrations of the metal; and Y is the peak stripping current value observed in step (b) for the metal.

2. The method of claim 1, wherein the iodine/iodide-based solution comprises at least one complexing agent selected from the group consisting of potassium iodide, sodium iodide, lithium iodide trihydrate, calcium iodide, and ammonium iodide.

3. The method of claim 1, wherein the iodine/iodide-based solution comprises iodine and potassium iodide.

4. The method of claim 1, wherein the concentration of the iodine/iodide-based solution is in the range of about 0.1M to about 1.0M for iodide in water and 0.01 to 0.5M for iodine.

5. The method of claim 1, wherein step (b) comprises setting up a potential to a working electrode in the iodide-based solution, followed by shifting the potential to a negative value which is sufficient to cause deposition of at least a portion of the metal onto the surface of the work in electrode, and then shifting the potential to a positive value which strips the metal from said surface.

6. The method of claim 5, wherein the shift in potential to the positive value is carried out by subjecting the working electrode to a positive scan in a pattern selected from the group consisting of linear scan, differential pulsed scan, and square-waved scan.

7. The method of claim 1, wherein step (b) is carried out by cyclic voltammetry or anodic stripping voltammetry.

8. The method of claim 1, wherein the metal being measured is selected from the group consisting of gold, silver, bismuth, cadmium, thallium, and mercury.

9. The method of claim 5, wherein a working electrode is made of gold, platinum or glassy carbon.

10. A method for detecting the presence of a metal contained in a sample, said metal being nonreactive with water, comprising the steps of:
    I) converting the metal present in the sample to a soluble metallic complex which is capable of being electrochemically analyzed by extracting the metal With an iodine/iodide solution; and
    II) setting up a positive potential for a working electrode in said iodine/iodide solution serving as the electrolyte of an electrolytic cell to obtain a clean surface of the working electrode shifting the potential to a negative value sufficient to cause deposition of at least a portion of the metal present onto the working electrode surface, and then shifting the potential to a positive value which strips deposited metal from the working electrode surface producing a measurable stripping current.

11. The method of claim 10, wherein the metal is selected from the group consisting of gold, silver, bismuth, cadmium, thallium, and mercury.

* * * * *